United States Patent [19]

Bernatets

[11] Patent Number: 4,750,367
[45] Date of Patent: Jun. 14, 1988

[54] DEVICE FOR EXAMINING MOVING OBJECTS BY MEANS OF ULTRASOUND ECHOGRAPHY

[75] Inventor: Jean-Luc Bernatets, Paris, France

[73] Assignee: U.S. Philips Corporation, New York, N.Y.

[21] Appl. No.: 7,144

[22] Filed: Jan. 27, 1987

[30] Foreign Application Priority Data

Jan. 31, 1986 [FR] France ............................. 86 01348

[51] Int. Cl.⁴ ........................................ G01N 29/06
[52] U.S. Cl. ..................................... 73/602; 128/660
[58] Field of Search .................... 73/602, 618, 629; 128/660

[56] References Cited

U.S. PATENT DOCUMENTS

| 4,163,249 | 7/1979 | Michael et al. | 358/21 R |
| 4,240,101 | 12/1980 | Michael et al. | 358/11 |
| 4,240,106 | 12/1980 | Michael et al. | 358/36 |
| 4,240,109 | 12/1980 | Michael et al. | 358/105 |
| 4,240,113 | 12/1980 | Michael et al. | 358/180 |
| 4,552,020 | 11/1985 | Auphan | 73/602 |
| 4,576,046 | 3/1986 | Fink et al. | 73/602 X |

OTHER PUBLICATIONS

Barnes, R. W. et al., An Ultrasound Digital . . . Use, IEEE Transactions, vol. SU-24, No. 6, Nov. '77, pp. 350-354.

Primary Examiner—Jerry W. Myracle
Attorney, Agent, or Firm—Jack E. Haken

[57] ABSTRACT

The device comprises at least one ultrasound transducer (10) which is connected to a transmitter stage (20) and to a stage (30) for receiving and processing echographic signals returned to the transducer. The latter stage (30) comprises a conventional first processing channel (60) which consists mainly of an amplifier circuit (61), an envelope detection circuit (62), a scan converter (64), and a display device (65), as well as a second processing channel (100), which comprises:

(A) an analog-to-digital converter (63) and a first image memory (641) for storing the image during acquisition;
(B) a motion detection circuit (130) which controls, or not, for each image point the application of a recursive temporal filtering coefficient $\alpha$;
(C) a conditional recursive temporal filter circuit (150) which supplies, on the output of said second processing channel (100), a treated image R(t, x, y) which forms a sum of the image I(t, x, y) most recently obtained and the preceding treated image R(t−1, x, y), weighted by values relating to said filter coefficient $\alpha$.

10 Claims, 1 Drawing Sheet

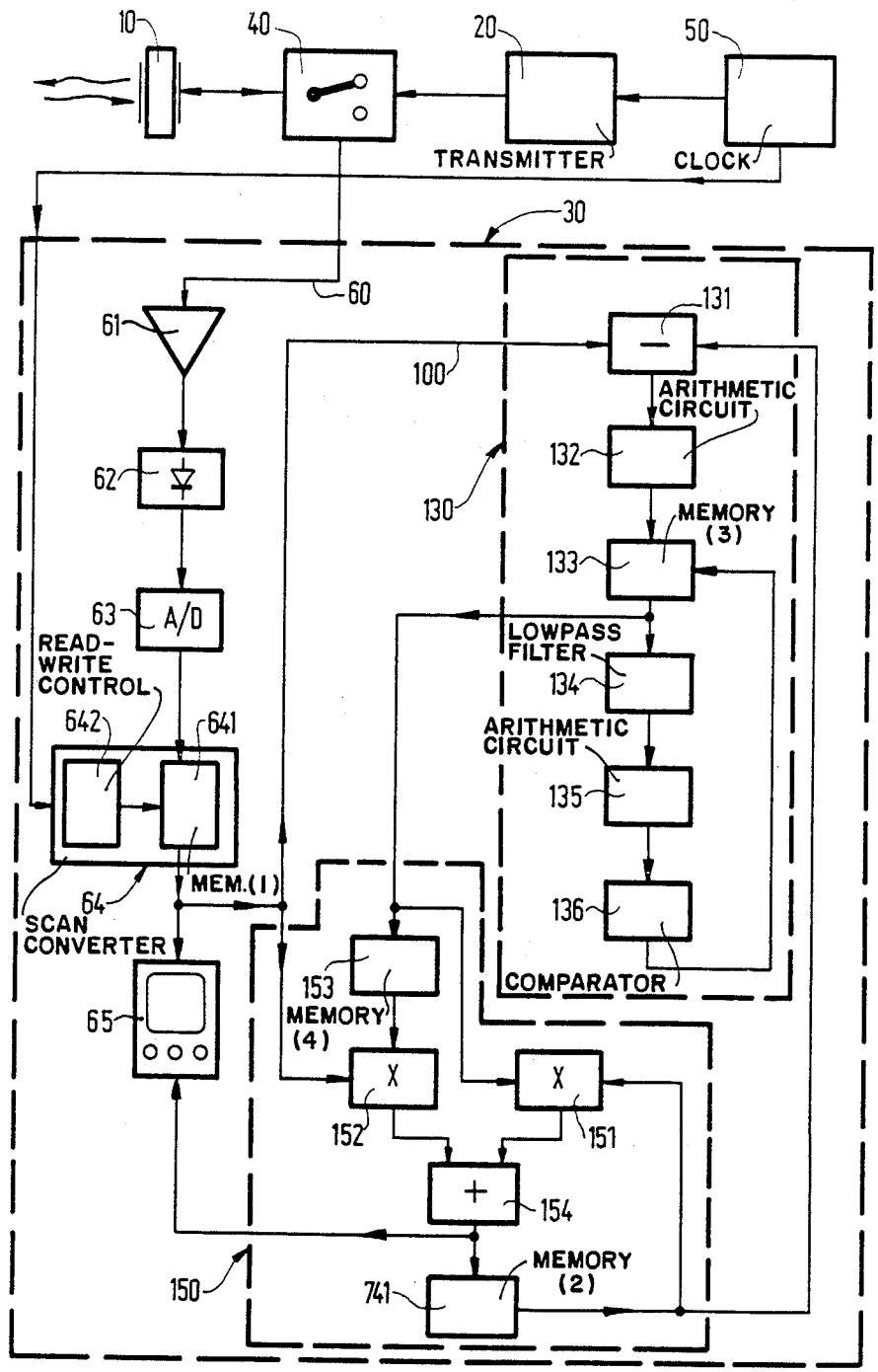

DEVICE FOR EXAMINING MOVING OBJECTS BY MEANS OF ULTRASOUND ECHOGRAPHY

The invention relates to a device for examining moving objects by means of ultrasound echography, comprising at least one ultrasound transducer which is connected to a transmitter stage for the repeated transmission of ultrasound signals to the object to be examined and to a receiver stage for receiving and processing echographic signals returned to said transducer, which receiver stage comprises a first processing channel which is composed mainly of an amplifier circuit, an envelope detection circuit, a scan converter, and a display device.

The execution of such an examination for making images of the heart is disclosed, for example in the article "Cardiac Ultrasonography" by D. L. King, published in Radiology 103, May 1972, pages 387 to 392. Ultrasound echography is actually one of the preferred methods of examining biological tissues because of its safety and capability of forming real-time images of the internal structures of organs. However, the quality of ultrasound images is often less than can be achieved by means of other imaging methods.

It is an object of the invention to propose an ultrasound echography device in which the possibility of real-time formation of the images is utilized for performing operations as a function of time in order to improve the quality of the images, without loss of spatial resolution due to either deterioration of the image components having a high spatial frequency or the motional unsharpness introduced by motions of the tissues or the organs.

To achieve this, a device of the kind set forth in accordance with the invention is characterized in that the receiver stage comprises a second processing channel which comprises:

(A) an analog-to-digital converter and a first image memory for the storage of an image obtained at an instant t in the form of data $I(t, x, y)$, x and y being the coordinates of the image points;

(B) a motion detection circuit which is suitable for updating, or not, for each image point a temporal recursive filter coefficient $\alpha$, depending on the value of difference between an obtained image point $I(t, x, y)$ and the corresponding point of an output image $R(t-1, x, y)$ of the second processing channel with respect to a given threshold value;

(C) a conditional temporal recursive filter which is suitable for producing, as the output signal of the second processing channel, a treated image $R(t, x, y)$ which consists of the sum of the weighted new obtained image $I(t, x, y)$ and the weighted, previously treated image $R(t-1, x, y)$, the weighting factors being dependent on the value of the filter coefficient $\alpha$. The analog-to-digital converter and the first image memory of the second processing channel preferably form part of the scan converter.

The proposed construction enables the detection of the zones of the image in which motions occur during a first period of time and the adaptation of the temporal operations to the detection of such motions during a second period, said operations being executed only if it can be assumed that no motions have taken place between one image and the next image.

In a special embodiment in accordance with the invention the motion detection circuit comprises a series connection of a subtractor for determining the difference between the value $I(t, x, y)$ originating from the first image memory and the value $R(t-1, x, y)$ originating from a second image memory, a third image memory for the alternating storage of said difference and the filter coefficient $\alpha$, a low-pass filter, and a comparator which is suitable for comparing the value of its input signal with a given threshold level and for generating, in dependence of the comparison result, an instruction for replacing the contents of the third image memory by a predetermined value which then constitutes the new filter coefficient $\alpha$.

The motion detection circuit in a further embodiment comprises a series connection of a subtractor for determining the difference between the value $I(t, x, y)$ originating from the first image memory and the value $R(t-1, x, y)$ originating from a second image memory, a third image memory for the alternating storage of said difference and the filter coefficient $\alpha$, a low-pass filter, and a fourth memory which is suitable for supplying an instruction for the replacement of the contents of the third image memory by a substitution value which is smaller as the value stored in the fourth memory is larger and vice versa, said substitution value then constituting the new filter coefficient $\alpha$.

In the above embodiments the temporal recursive filter may comprise a first multiplier for multiplying the filter coefficient $\alpha$ by the output signal of the first or the third image memory, and a second multiplier for multiplying the one's complement $-\alpha$ of the filter coefficient by the output signal of the third or the first image memory, as well as an adder for adding the output signals of said multipliers and the second image memory for the storage of the images treated by the temporal recursive filter.

All image points can be treated successively by means of a single second processing channel, or in parallel by means of as many processing channels as there are points. Alternatively, a compromise between these two solutions can be used which involves a plurality of parallel connected second processing channels, each of which serves for the successive treatment of a corresponding part of the points.

The invention will be described in detail hereinafter with reference to the drawing which shows a block diagram of an embodiment in accordance with the invention.

The present embodiment of the device includes an ultrasound transducer 10 whereto there are connected on the one hand a transmitter stage 20 for the repeated transmission of ultrasound signals to the object to be examined, and on the other hand a receiver stage 30 for the reception and further processing of the echographic signals returned to the transducer. Between the transmitter stage and the receiver stage there may be connected a switching stage 40 in order to prevent notably overloading of the receiver stage by the transmitter stage; similarly, a safety circuit (not shown) may preceed the receiver stage for the same purpose.

A clock circuit 50 controls the sequencing in a conventional manner by determining on the one hand the repetition rhythm of the image with a frequency in the order of magnitude of, for example from 8 $H_z$ to 40 $H_z$ and on the other hand the repetition rhythm of the image lines (approximately 128 image lines per image). For each new image the transducer 10 is reset to its initial state, after which it again scans the entire region to be examined one line after the other. For each image line a first processing channel 60 receives electric signals from the transducer 10 in accordance with the echographic signals returned to the transducer. These signals are amplified in an amplifier 61 and are subsequently rectified and filtered in an envelope detector 62 before being displayed on a display device 65.

In order to enable such display, the envelope signals are digitized in an analog-to-digital converter 63, after which they are applied to a scan converter 64. The converter 64 actually comprises a first image memory 641 in which the values of the image points are written. A write/read circuit 642 controls on the one hand the write operations and on the other hand the read operations in the image memory for the display of the image stored.

In accordance with the invention, the device also comprises a second processing channel 100 which is formed by a motion-detection circuit 130 whose operation is based on the comparison of successive images, and a conditional temporal recursive filter 150.

The motion detection circuit 130 comprises a subtractor 131 which is suitable for calculating for each image point the difference between an image point most recently obtained by the scan converter 64 and the corresponding point associated with the previously displayed image point and stored in a second temporary image memory 741. The difference is applied to a third image memory 133, a low-pass filter 134 being connected to the output thereof. The filtering thus realized serves to eliminate isolated points which are caused by random noise and which must be eliminated. The filtering operation may notably be a spatial filtering operation which is performed, for example by replacing each image point by an arithmetical mean value of image points in a window of n×n image points centred about the relevant image point (in this case n=3). The spatial filtering of an image is well known and will not be elaborated upon herein The output signal of the low-pass filter 134 is applied to a comparator 136 which imposes a threshold for each successive point of the filtered image. When the filtered signal has an absolute value for a given point which is smaller than or equal to the threshold level, it is decided that no motions have occurred in the vicinity of this point and that a filtering operation performed between the images can be performed. However, if the filtered signal has an absolute value which is higher than said threshold level, it is decided that motions have occurred and that this (temporal) filtering operation performed between the images as a function of time must not be performed. In accordance with the comparison result thus obtained, the data stored in the third image memory 133 is updated, by substitution of the value "zero" (motions) or a predetermined coefficient (absence of motions), for the value originally present in this memory (and used for the calculation of the value received by the comparator).

The output signal of the third memory 133, being referred to hereinafter as the filter coefficient α, is applied to the conditional temporal recursive filter 150. As has already been described, this filtering operation between an image already obtained at the instant (t−1) and an image obtained at the instant t is performed without going into the actual nature of the time interval (t−1, t). In order to abbreviate the term "image point", the expression "pixel" will be used hereinafter, each pixel being denoted by its position (x, y) in each image. When the originally obtained image, depending on x, y and the instant t, is referred to as I(t, x, y), when the image obtained as a result of the temporal recursive filtering is referred to as R(t, x, y) and when the reference α denotes a coefficient which represents the filter effectiveness and which amounts to from 0 to 1, it may be stated that said filtering operation can be performed in accordance with the following expression:

$$R(t, x, y) = \alpha(t, x, y) \cdot R(t-1, x, y) + (1 - \alpha(t, x, y)) \cdot I(t, x, y).$$

It appears from this expression that α actually determines the effectiveness of filtering because:

for a small value of α the images are filtered to only a small extent because the term $(1\alpha) \cdot I$ prevails (and when α is very small, the images are almost not filtered at all, which is the same as ineffective filtering):.

for a large value of α, however, the term $\alpha \cdot R$ prevails, but when α is too large, this term dominates to such an extent, that the information contained in the last image I(t, x, y) obtained is almost completely neglected, so that only the effect of the first image treated is taken into account, which is again the same as ineffective filtering.

In order to achieve correct filtering in practice, therefore, a suitable value must be chosen for α. Tests have demonstrated that $(1-\alpha)$ must be approximately equal to the reciprocal value of the number of images required to ensure that the treatment is noticeable, and that a value of α equal to $\frac{7}{8}$ is a suitable choice in this respect.

The conditional temporal recursive filter 150, thus being connected to the output of the third image memory 133, comprises a first multiplier 151 which receives the output signal of the third memory 133, and a second multiplier 152 which, due to the presence of a fourth memory 153, receives the one's complement of the coefficient α calculated for each pixel by the motion detection circuit 130. For each value of said coefficient used as an address, the fourth memory 153 contains the value of the desired one's complement. The multiplier 151 serves to multiply the output signal of the second image memory 741 (which means the image R(t−1) treated during the preceding period and displayed after this operation) by the output signal of the third memory 133, and the multiplier 152 serves to multiply the output signal of the first image memory 641 of the scan converter 64 (which means the newly formed image I(t)) by the one's complement (originating from the fourth memory 153) of the same output signal of the third memory 133. It would alternatively be possible to perform symmetrical multiplications of the output signal of the memory 641 by the output signal of the memory 133 and of the output signal of the memory 741 by the one's complement of the output signal of the memory 133.

The circuit 150 also comprises an adder 154 which receives the output signals of the two multipliers 151 and 152 and which supplies a signal which satisfies the above expression:

$$R(r) = \alpha \cdot R(t-1) + (1-\alpha) \cdot I(t).$$

The output signal of this adder 154 is applied to the display device 65 and also to the second image memory 741 which temporarily stores the image thus received; this image is subsequently upon arrival of the newly formed image I(t) referred to as the preceding image R(t−1). This temporary storage of the treated image is required until the treatment of the next image has been completed, i.e. the new image now being formed.

Using the notations adopted above, it appears that the motion detection circuit 130 described in detail above and preceding the conditional temporal recursive filter 150 determines the difference in the subtractor 131 between the signals I(t) of the newly obtained image and R(t−1) of the preceding image, treated by means of a conditional filtering operation and displayed, in view of later conditional filtering operations in the circuit 150 which will lead to the determination of a new treated image R(t), which itself will be subtracted from I(t+1) in the subtractor 131, and so on.

It will be apparent that the present invention is not restricted to the described embodiment, because many variations thereof can be proposed without departing from the scope of the present invention.

It will notably be apparent that the device in accordance with the invention may comprise not only a single transducer, but also a linear or two-dimensional array of transducers which may be connected to an electronic scanning device.

Furthermore, during the detection of motions by the circuit 130 the difference between successive images may be replaced by a quantity which is a function of this difference, for example by the square thereof or by a more complex function. This quantity is then calculated in all cases by means of a first arithmetic circuit 132 which is connected to the output of the subtractor 131 and which will generally consist of a read-only memory which outputs the value of said quantity which corresponds to the difference signal on the output of the subtractor. Similarly, a second arithmetic circuit 135 may be connected to the output of the low-pass filter 134 in order to replace the output value of this filter by a function relating to this value, for example the absolute value of this output value. When the one of these arithmetic circuits 132 and 135 is used, or both, it will be apparent that the output signal of the circuit 132 is applied to the third image memory 133 and the output signal of the circuit 135 is applied to the comparator 136.

In an alternative embodiment, the comparator 136 may be replaced by an arithmetic circuit of the "readonly memory" type which, in accordance with the result of the comparisons can either supply instruction for exactly the same substitution operations as used above, or a substitution value for storage in the third image memory 133, said substitution value being smaller as the contents of the memory is larger and vice versa. In the latter case instead of a comparison on the basis of all or nothing, there is performed a filtering operation as a function of time between the images, said filtering operation being less extensive as the probability of occurrence of a motion at the area of the pixel considered is higher, or vice versa. This gradually increasing or decreasing filter operation can be performed, for example, by gradually varying the value of $\alpha$, being the coefficient of effectiveness of filtering, as a function of a larger or smaller assumed motion instead of restricting it to a binary choice ($\frac{7}{8}$ if no motions are detected and zero if motions are detected).

It is also to be noted that various alternatives exist for the embodiments of all means used for the point-by-point execution of the operations. Actually, these operations can be successively executed point-wise by a single circuit. However, they can also be executed in parallel by as many circuits as there are pixels in the image (for example 256×256); this solution accelerates the operation to a high degree, but substantially increases the complexity of the circuits of the device. Finally, these operations can also be performed by means of a compromise between the two foregoing solutions where a plurality of circuits are connected in parallel for the successive treatment of each time a part of the points.

It is also to be noted that, in the case of echocardiography or examination of a cyclically moving organ, an apparatus in which the above invention is used should save all images of a complete cycle in the memory; in the case of a cardiac cycle, this means the images over a period of approximately 1 second. Because a high-quality echography device for cariographic examinations produces approximately fifty images per second, such storage of images could be problematic. In this respect two solutions are feasible, that is to say either extending the device with a digital memory disc having a high capacity and a high accessibility, or the use of an adequate number of image memories. Such a disc or such image memories are commercially available. A third solution consists in reducing the capacity of the memory required. A reduced performance can indeed be accepted from the apparatus in accordance with the invention, its capability then being restricted to the treatment of a limited number of images instead of all images of the cardiac cycle, for example to the treatment of images relating to preferred instants marked in the echocardiogram (for example, the end of the systole, the end of the diastole, complications clearly indicated in the echocardiogram etc). However, in order to enable the determination of such preferred instants, synchronization with respect to the cycle to be observed is required. Such synchronization is described for other types of cardiac examinations in U.S. Pat. No. 4,547,892 and will not be elaborated herein. Because the motions of the heart and the thorax are substantially periodical, this synchronization is realized so that the various parts of the organ examined are situated in substantially the same position during each cycle. As a result of this characteristic property, the filtering operation as a function of time can be performed in accordance with the invention without necessitating the elimination of detection of motion effects.

What is claimed is:

1. In a device for examining moving objects by means of ultrasound echography, comprising at least one ultrasound transducer which is connected to transmitter means for the repeated transmission of ultrasound signals to the object to be examined and to receiver means for receiving and processing echographic signals returned to said transducer, which receiver means comprise a first processing channel which includes an amplifier circuit, an envelope detection circuit, a scan converter, and a display device, the improvement wherein the receiver means further includes a second processing channel which comprises:

(A) an analog-to-digital converter and a first image memory which store an image obtained at an instant t in the form of data I(t, x, y), x and y being the coordinates of image points;

(B) motion detection means which for each image point selectively update a temporal recursive filter coefficient $\alpha$, depending on the value of the difference between an obtained image point I(t, x, y) and the corresponding point of an output image R(t−1, x, y) of the second processing channel, with respect to a given threshold value;

(C) a conditional temproal recursive filter which produces, as the output signal of the second processing channel, a treated image A(t, x, y) which consists of the sum of the weighted new obtained image I(t, x, y) and the weighted, previously treated image R(t−1, x, y), the weighting factors being dependent on the corresponding value of said filter coefficient $\alpha$.

2. A device as claimed in claim 1, wherein the analog-to-digital converter and the first image memory are included within the scan converter.

3. A device as claimed in claims 1 or 2, further comprising: a second image memory which stores the output of the temporal recursive filter wherein the motion detection means comprises a series connection of a subtractor which determines the difference between the value I(t, x, y) which originates from the first image memory and the value R(t−1, x, y) which originates from the second image memory; a third image memory for alternating storage of said difference and the filter coefficient $\alpha$, a low-pass filter, and comparator means which compare the value of its input signal with a given threshold level and generate, in dependence of the comparison result, an instruction for replacing the contents of the third image memory by a predetermined value which then constitutes the updated filter coefficient $\alpha$.

4. A device as claimed in claim 3, wherein the temporal recursive filter comprises a first multiplier which multiplies the filter coefficient $\alpha$ by the output signal of the first or the third image memory, a second multiplier which multiplies a one's complement 1−$\alpha$ of the filter coefficient by the output signal of the third or the first image memory, and an adder which adds the output signals of said multipliers and the second image memory.

5. A device as claimed in claim 3 wherein the second processing channel comprises a first arithmetic circuit which is connected to the subtractor and which determines a quantity which is a function of the output signal of said subtractor and forms the filter coefficient $\alpha$ for storage in the third image memory.

6. A device as claimed in claim 5, wherein the first and the second arithmetic circuits comprise read-only memories.

7. A device as claimed in claim 3 wherein the second processing channel comprises a second arithmetic circuit which is connected to the output of the low-pass filter, which determines a quantity which is a function of the output signal of said filter and which forms the new value of the signal for comparison with a given threshold level.

8. A deice as claimed in claim 7, wherein the first and the second arithmetic circuits comprise read-only memories.

9. A device as claimed in claims 1 or 2, further comprising a second image memory which stores the output of the temporal recursive filter wherein the motion detection means comprises a series connection of a subtractor which determines the difference between the value I(t, x, y) which originates from the first image memory and the value R(t−1, x, y) which originates from the second image memory; a third image memory for alternating storage of said difference and the filter coefficient $\alpha$, a low-pass filter, and a fourth memory which supplies an instruction for the replacement of the contents of the third image memory with a substitution value which becomes smaller as the value stored in the fourth memory becomes larger and vice versa, said substitutuion value constituting the updated filter coefficient $\alpha$.

10. A device as claimed in claim 4, wherein the temporpal recursive filter comprises a first multiplier which multiplies the filter coefficient $\alpha$ by the output signal of the first or the third image memory, a second multplier which multiplies a one's complement 1—$\alpha$ of the filter coefficient by the output signal of the third or the first image memory, and an adder which adds the output signals of said multipliers and the second image memory.

* * * * *